United States Patent [19]

Wolcott et al.

[11] 4,333,810

[45] Jun. 8, 1982

[54] ANALYZER FOR CHEMICAL OXIDIZING OR REDUCING AGENTS

[75] Inventors: Duane K. Wolcott; John B. Carraway, Jr., both of Baton Rouge, La.

[73] Assignee: The Dow Chemical Company, Midland, Mich.

[21] Appl. No.: 139,379

[22] Filed: Apr. 11, 1980

[51] Int. Cl.³ .................. G01N 27/30; G01N 27/52
[52] U.S. Cl. .................. 204/195 M; 204/1 T; 204/195 R
[58] Field of Search .................. 204/195 M, 1 B, 296, 204/195 R

[56] References Cited

U.S. PATENT DOCUMENTS

| | | | |
|---|---|---|---|
| 2,850,640 | 9/1958 | Dudley et al. | 250/43.5 |
| 3,031,385 | 4/1962 | Johnson et al. | 204/1 T |
| 3,421,989 | 1/1969 | Haagen-Smit | 204/195 H |
| 3,486,997 | 12/1969 | Petersen | 204/195 F |
| 3,562,139 | 2/1971 | Leitz | 204/296 |
| 3,634,213 | 1/1972 | Coates | 204/296 X |
| 3,713,994 | 1/1973 | Shults et al. | 204/1 T |
| 3,761,377 | 9/1973 | Mang | 204/195 R |
| 3,824,171 | 7/1974 | Houwelingen et al. | 204/195 M |
| 3,852,169 | 12/1974 | Kring et al. | 204/1 T |
| 3,857,777 | 12/1974 | Guilbault et al. | 204/296 |
| 3,902,982 | 9/1975 | Nakagawa | 204/195 R |
| 3,996,123 | 12/1976 | Kruishoop | 204/195 R |
| 4,176,215 | 11/1979 | Molnar et al. | 204/296 X |

OTHER PUBLICATIONS

XR Perfluorosulfonic Acid Membranes, Du Pont de Nemours & Co., Oct. 1, 1969.
Perfluorinated Ion Exchange Membranes, 141st Nat. Meeting, The Electrochem. Soc., (1972).

*Primary Examiner*—G. L. Kaplan
*Attorney, Agent, or Firm*—A. J. Young

[57] ABSTRACT

An analyzer for the quantitative determination of a chemical oxidizing or reducing agent in a fluid environment. The analyzer includes a novel type of sensor or detector comprising a first electrode exposed to the fluid environment; a second electrode in contact with a solution of electrolyte; and an ion-exchange membrane to contain the electrolyte solution, and to separate the second electrode from the fluid environment and the first electrode.

27 Claims, 4 Drawing Figures

ANALYZER FOR CHEMICAL OXIDIZING OR REDUCING AGENTS

BACKGROUND OF THE INVENTION

This invention relates to the quantitative determination of chemical oxidizing and reducing agents in a fluid environment. More particularly, the invention relates to the determination of chemical oxidizing and reducing agents by means of a novel type of sensor or detector which includes an ion-exchange membrane.

In the current state of the art, the electrodes forming a part of the electrochemical cell or couple in analyzers are separated from each other by means of a porous layer. The porous layer permits a restricted flow of electrolyte, thereby completing the electrochemical couple between the electrodes in the sensor portion of the analyzers. A serious disadvantage of the porous layer is that it permits a substantial diffusion of sample throughout the electrolyte between the electrodes. As a result, the recovery time necessary to stabilize known analyzers between tests is relatively long, and the only known way to reduce the recovery time is to provide special means of renewing the electrolyte in the analyzers. These special means are not entirely satisfactory in that they are cumbersome, costly, and require frequent and extensive maintenance. The present invention provides an analyzer which is not subject to the limitations of lengthy recovery time or the necessity of providing auxiliary means for re-stabilizing the electrode system.

A second serious disadvantage of the porous layer is that it is non-selective. The porous layer permits the electrodes to be exposed to all constituents of the fluid being monitored. The result is the possibility of contamination or poisoning of the electrodes, and of direct interference in the quantitative measurement by substances present in the sample other than those being determined. The present invention provides a means which, in combination with the electrodes, substantially eliminates the possibility of contamination or poisoning of the electrodes and of interference by extraneous components of the environment being tested.

SUMMARY

In general, this invention provides an instrument for the quantitative determination of chemical oxidizing and reducing agents in a fluid environment. The instrument includes a first electrode exposed to the fluid environment being tested; a second electrode, in contact with a solution of electrolyte; an ion-exchange membrane adapted to contain the electrolyte solution, said membrane separating the electrolyte and second electrode from the first electrode; said first electrode and membrane being in electrical contact, thereby completing the electrochemical couple between the first and second electrodes; and means for measuring a flow of electrical current generated between the electrodes.

The choice of membrane depends upon the chemical species being quantitatively determined. If an oxidizing species such as a halogen is to be determined, a cation-exchange membrane is chosen to permit a flow of positive ions from the electrolyte through the membrane to the first electrode. If a reducing species such as hydrogen, carbon monoxide or hydrogen sulfide is to be determined, an anion-exchange membrane may be used to permit a flow of negative ions from the electrolyte through the membrane to the first electrode.

The function of the instrument may be classified as electrochemical in nature. If the first and second electrodes are made of dissimilar metals, the first electrode is characterized as being catalytic with respect to the oxidizing or reducing agent being determined but chemically inert to the agent and fluid environment in which it is positioned, and the second electrode is characterized as being chemically reactive in the electrolyte solution and being consumed by the electrochemical reaction taking place during determination of the agent. If the first and second electrodes are made of the same metal, they are characterized as both being catalytic to the agent being determined and chemically inert to the environments in which they are positioned. Also, if both electrodes are made from the same metal, an additional means is required for imposing a voltage across and causing direct electrical current to flow between the electrodes, thereby providing the driving force for the electrochemical reaction of the instrument. If the electrodes are made of dissimilar metals, an additional power source is not necessarily required since a galvanic couple will be formed between the electrodes. However, an external power source may be used if desired. For example, an external power source may be used in the case where the galvanic potential is insufficient as a driving force for the electrochemical reaction to provide an accurate readout for the instrument or where it is desired to decrease the rate of the electrochemical reaction, thereby increasing the effective range of the instrument.

It is an object of this invention to provide a compact, sensitive instrument for the determination of chemical oxidizing and reducing agents. It is a further object to provide apparatus which is characterized by a relatively short time of recovery between tests. Other objects of the invention will be apparent to those skilled in the art from the more detailed description which follows.

DESCRIPTION OF THE PREFERRED EMBODIMENTS

The following description illustrates the manner in which the principles of the invention are applied, but it is not to be construed as in any way limiting the scope of the invention.

Figures 1, 2:
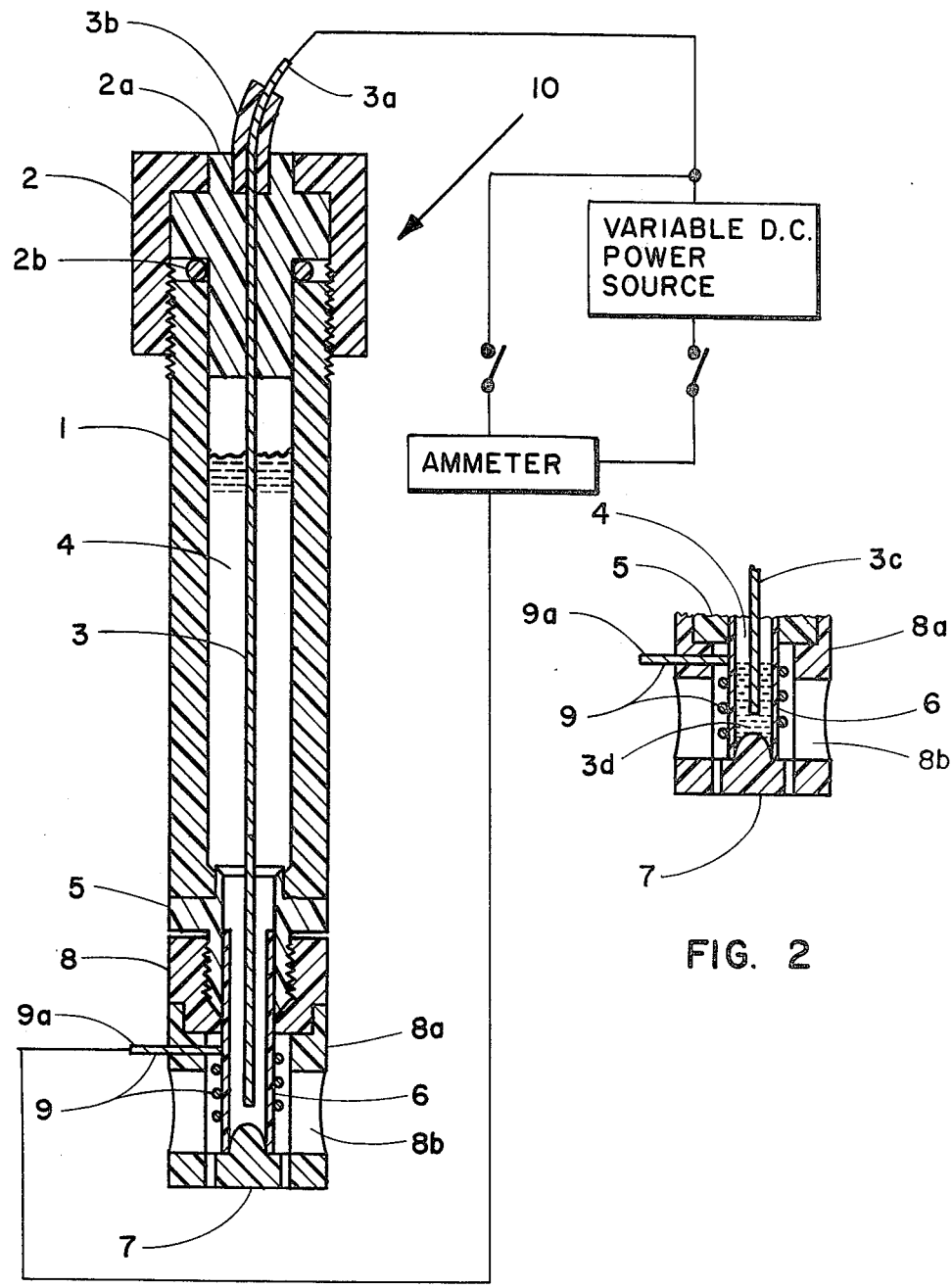
FIG. 1 is a cross-sectional view of a detector constructed according to the principles of the present invention.
FIG. 2 is a partial cross-sectional view of a detector illustrating a modification of the detector shown in FIG. 1 according to the principles of the present invention.

More specifically, referring to FIG. 1, a detector or sensor 10 is illustrated. The sensor 10 comprises a hollow cylindrical body 1 adapted to contain an electrolyte solution 4; a means for sealing the body 1 at the top which includes a threaded cap 2, an electrically-insulating member 2a, and an "O" ring 2b; means for sealing the body 1 at the bottom which includes a swagelock fitting 5, a tube 6 formed from an ion-exchange membrane material, and an end plug 7 fitted into and sealing the end of the tube 6; a nut 8 threaded onto the swagelock fitting 5; a lower cap 8a for protecting the tube 6 secured to the nut 8 which includes openings 8b; an electrode 3 in contact with the electrolyte solution 4 and extending into the tube 6, said electrode 3 having a terminal end connection 3a and being covered with electrical insulation 3b; and an electrode 9 wound around tube 6 and having a terminal end connection 9a.

Referring to FIG. 2, a modified version of the sensor 10 shown in FIG. 1 is illustrated. The modified version of the sensor 10 includes a mercury pool electrode 3d in electrical contact with an electrical-lead wire 3c. All other elements of sensor 10 remain unchanged.

The electrolyte solution 4 is generally a solution of an inorganic halide. Preferably, the electrolyte solution 4 is a saturated aqueous solution of calcium chloride or lithium chloride. In addition, the electrode 3 is preferably a silver wire and electrode 9 is preferably a platinum wire when the electrodes are made from dissimilar metals. When the electrodes are made from the same metal, both electrodes 3 and 9 are preferably made of platinum. In the modified version of the sensor 10 shown in FIG. 2, the electrical-lead wire 3c in contact with the mercury pool electrode 3d is preferably made of platinum. The tube 6 can be formed from any known ion-exchange membrane material depending on the requirements of the sensor 10. Preferably, if a cation-exchange membrane is desired, the tube 6 is beneficially made from a material having a polytetrafluoroethylene backbone and perfluorinated two-carbon sulfonated sidechains such as that marketed by E. I. du Pont de Nemours and Company, Inc., under the tradename "Nafion". If an anion-exchange membrane is desired, the tube 6 is beneficially made from a styrenedivinyl-benzene copolymer having quaternary-ammonium sidechains. The remaining structural elements of the sensor 10 can be constructed of any known structural material which will also provide electrical insulation for the electrochemical circuit. For example, a plastic material such as chlorinated polyvinylchloride may beneficially be used.

To complete the analyzer, any known means (not shown) for accurately measuring the flow of electrical current is connected between the terminal end connections 3a and 9a of the sensor 10. For example, a microammeter or a resistor in parallel combination with a voltmeter may beneficially be used. A suitable measuring device includes a ten-thousand ohm resistor in parallel combination with a Hickok LX-303 Digital Voltmeter. If a source of voltage and direct electric current is imposed on the electrodes, this source may be any well-known means such as a battery or an alternating power source which has been stepped down with a direct current transformer or rectifier. A chart recorder may also be beneficially used in combination with the current measuring means to provide a permanent and continuous record. The current measuring means is also preferably adapted to read out directly in the quantity of the chemical oxidizing or reducing agent detected in the test environment.

A particularly preferred use of the sensor 10 is for measuring the concentration of a halogen such as chlorine in air. Before using a new sensor 10 for measuring the chlorine content in air, it has been found that it is preferable to pre-condition the sensor 10 to improve its sensitivity. Pre-conditioning is accomplished by making a direct electrical connection between the terminal end connections 3a and 9a, and then exposing the electrode 9 to an atmosphere of substantially pure wet chlorine gas for a period of ten to fifteen minutes. The exact reason that the sensitivity of the sensor 10 is improved by pre-conditioning is not known, but it is theorized that pre-conditioning brings a new sensor 10 to a faster chemical equilibrium across the electrochemical couple of the electrodes 3 and 9, the electrolyte solution 4 and the ion-exchange tube 6.

Figure 3:
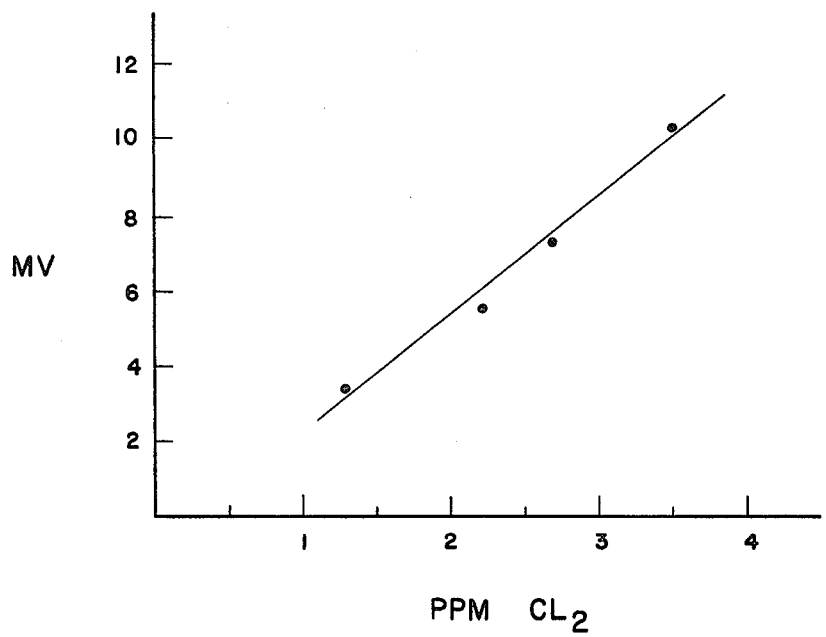
FIGS. 3 and 4 illustrate typical response curves for detectors constructed according to the principles of the present invention.
Figure 4:
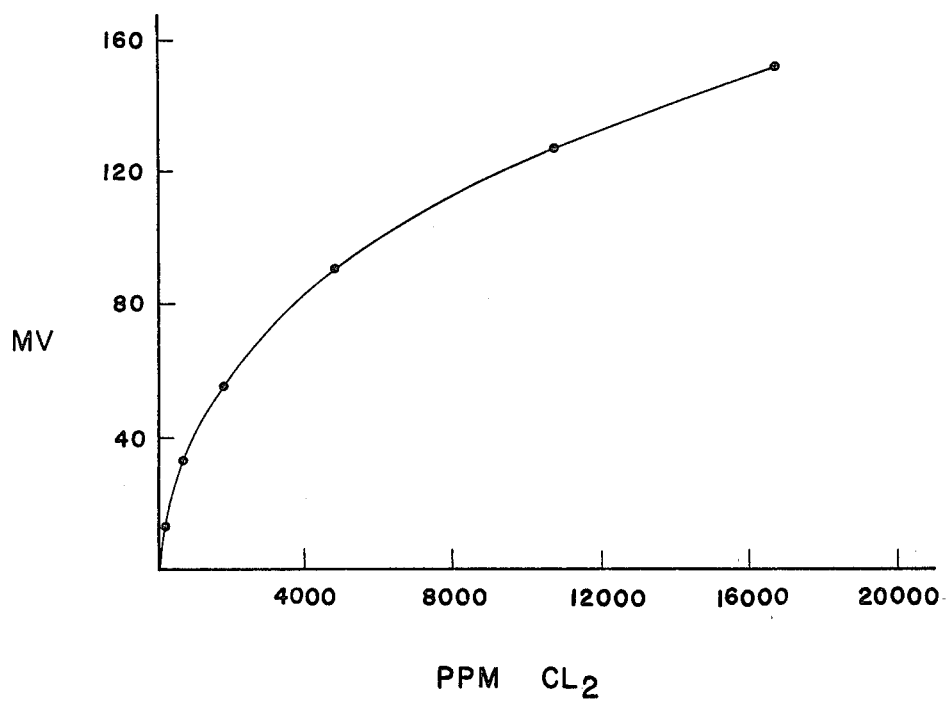

To further illustrate the present invention a series of four test runs were made with the present sensor to determine the chlorine concentration (expressed as parts per million) in air. In each run the chlorine concentration was known and the readout in millivolts was reproducibly determined. The results of the runs are shown in the following Table 1, and are further illustrated by representative curves for Run No. 1 and Run No. 4 shown in FIGS. 3 and 4, respectively. In Runs 1, 2 and 3, the current-measuring device was a ten-thousand ohm resistor in parallel combination with a Hickok XL-303 Digital Voltmeter. In Run No. 4, the current-measuring device was a four-hundred and fifty ohm resistor in parallel combination with a voltmeter/stripchart recorder. In Run No. 1, a sensor, as illustrated by FIG. 2, including platinum and mercury pool electrodes and a saturated calcium chloride electrolyte solution, was used. In Run No. 2, a sensor, as illustrated by FIG. 1, including platinum and silver electrodes and a saturated lithium chloride electrolyte solution, was used. In Run No. 3 and Run No. 4, a sensor, as illustrated by FIG. 1, including platinum and silver electrodes and a saturated calcium chloride electrolyte solution, was used. In all four runs, a cation-exchange membrane tube was used which was made from a material having a polytetrafluoroethylene backbone and perfluorinated two-carbon sulfonated sidechains sold under the tradename "Nafion" by E. I. du Pont de Nemours and Company, Inc.

TABLE 1

| $Cl_2$ - PPM | MILLIVOLTS | | | |
|---|---|---|---|---|
| | RUN #1 | RUN #2 | RUN #3 | RUN #4 |
| 1.3 | 3.4 | 14.3 | 6.3 | — |
| 2.2 | 5.5 | 16.8 | 7.6 | — |
| 2.7 | 7.3 | 20.7 | 9.8 | — |
| 3.5 | 10.2 | 25.3 | 13.6 | — |
| 158 | — | — | — | 13.9 |
| 644 | — | — | — | 30.3 |
| 1,856 | — | — | — | 56.0 |
| 4,876 | — | — | — | 90.8 |
| 10,860 | — | — | — | 128.0 |
| 16,773 | — | — | — | 152.0 |

While certain representative embodiments and details have been shown for the purpose of illustrating this invention, it will be apparent to those skilled in the art that various changes and modifications can be made therein without departing from the spirit and scope of the invention. For example, while particular attention has been directed toward the determination of gaseous species, the scope of the invention is by no means limited thereto. Liquids and solutions which contain oxidizing or reducing agents also fall within the scope of the invention.

What is claimed is:

1. An instrument for quantitatively determining the concentration of chemical oxidizing and reducing agents in a gaseous environment, comprising: a first electrode exposed to said gaseous environment; a second electrode; an electrolyte solution; an ion-exchange membrane adapted to contain said electrolyte solution; and means for measuring a flow of electrical current generated between said first and second electrodes, said second electrode in contact with said electrolyte solution, said ion-exchange membrane separating said electrolyte solution and second electrode from said first electrode, said first electrode in electrical contact with said ion-exchange membrane thereby completing an electrochemical couple between said first and second electrodes.

2. The instrument of claim 1 wherein said first and second electrodes are formed from dissimilar metals.

3. The instrument of claim 2 wherein said ion-exchange membrane is a cation-exchange membrane, whereby said instrument is adapted to quantitatively determine the concentration of a chemical oxidizing agent in the gaseous environment.

4. The instrument of claim 3 wherein said cation-exchange membrane is formed from a material having a polytetrafluoroethylene backbone and perfluorinated two-carbon sulfonated sidechains.

5. The instrument of claim 2 wherein said ion-exchange membrane is an anion-exchange membrane, whereby said instrument is adapted to quantitatively determine the concentration of a chemical reducing agent in the gaseous environment.

6. The instrument of claim 5 wherein said anion-exchange membrane is formed from a styrene-divinyl-benzene copolymer having quaternary-ammonium sidechains.

7. The instrument of claim 1 wherein said first and second electrodes are formed from the same metal, and said instrument includes a means for imposing a voltage across and flow of direct electrical current between said first and second electrodes.

8. The instrument of claim 7 wherein said ion-exchange membrane is a cation-exchange membrane, whereby said instrument is adapted to quantitatively determine the concentration of a chemical oxidizing agent in the gaseous environment.

9. The instrument of claim 8 wherein said cation-exchange membrane is formed from a material having a polytetrafluoroethylene backbone and perfluorinated two-carbon sulfonated sidechains.

10. The instrument of claim 7 wherein said ion-exchange membrane in an anion-exchange membrane, whereby said instrument is adapted to quantitatively determine the concentration of a chemical reducing agent in the gaseous environment.

11. The instrument of claim 10 wherein said anion-exchange membrane is formed from a styrene-divinyl-benzene copolymer having quaternary-ammonium sidechains.

12. The instrument of claim 2 wherein said instrument includes a means for imposing a voltage across and flow of direct electrical current between said first and second electrodes.

13. The instrument of claim 12 wherein said ion-exchange membrane is a cation-exchange membrane, whereby said instrument is adapted to quantitatively determine the concentration of a chemical oxidizing agent in the gaseous environment.

14. The instrument of claim 13 wherein said cation-exchange membrane is formed from a material having a polytetrafluoroethylene backbone and perfluorinated two-carbon sulfonated sidechains.

15. The instrument of claim 12 wherein said ion-exchange membrane is an anion-exchange membrane, whereby said instrument is adapted to quantitatively determine the concentration of a chemical reducing agent in the gaseous environment.

16. The instrument of claim 15 wherein said anion-exchange membrane is formed from a styrene-divinyl-benzene copolymer having quaternary-ammonium sidechains.

17. A sensor adapted for use in an instrument utilized to quantitatively determine the concentration of chemical oxidizing and reducing agents in a gaseous environment, comprising: a first electrode exposed to said gaseous environment; a second electrode; an electrolyte solution; and an ion-exchange membrane adapted to contain said electrolyte solution, said second electrode in contact with said electrolyte solution, said ion-exchange membrane separating said electrolyte solution and second electrode from said first electrode, said first electrode in electrical contact with said ion-exchange membrane, thereby completing an electrochemical couple between said first and second electrodes.

18. The sensor of claim 17 wherein said first and second electrodes are formed from dissimilar metals.

19. The sensor of claim 18 wherein said ion-exchange membrane is a cation-exchange membrane, whereby said instrument is adapted to quantitatively determine the concentration of a chemical oxidizing agent in the gaseous environment.

20. The sensor of claim 19 wherein said cation-exchange membrane is formed from a material having a polytetrafluoroethylene backbone and perfluorinated two-carbon sulfonated sidechains.

21. The sensor of claim 18 wherein said ion-exchange membrane is an anion-exchange membrane, whereby said instrument is adapted to quantitatively determine the concentration of a chemical reducing agent in the gaseous environment.

22. The sensor of claim 21 wherein said anion-exchange membrane is formed from a styrene-divinyl-benzene copolymer having quaternary-ammonium sidechains.

23. The sensor of claim 17 wherein said first and second electrodes are formed from the same metal.

24. The sensor of claim 23 wherein said ion-exchange membrane is a cation-exchange membrane, whereby said instrument is adapted to quantitatively determine the concentration of a chemical oxidizing agent in the gaseous environment.

25. The sensor of claim 24 wherein said cation-exchange membrane is formed from a material having a polytetrafluoroethylene backbone and perfluorinated two-carbon sulfonated sidechains.

26. The sensor of claim 23 wherein said ion-exchange membrane is an anion-exchange membrane, whereby said instrument is adapted to quantitatively determine the concentration of a chemical reducing agent in the gaseous environment.

27. The sensor of claim 26 wherein said anion-exchange membrane is formed from a styrene-divinyl-benzene copolymer having quaternary-ammonium sidechains.

* * * * *